(12) United States Patent
Wyrobnik et al.

(10) Patent No.: US 10,624,954 B2
(45) Date of Patent: *Apr. 21, 2020

(54) AGENT FOR REDUCING THE USEABLE CALORIE CONTENT OF FOOD AND FOR THERAPEUTIC REDUCTION OF WEIGHT, IN PARTICULAR FOR USE IN THE CASE OF ADIPOSITY (OBESITY)

(71) Applicant: PRO NATURA GESELLSCHAFT FUR GESUNDE ERNAHRUNG MBH, Frankfurt am Main (DE)

(72) Inventors: Daniel Henry Wyrobnik, Frankfurt am Main (DE); Isaac Harry Wyrobnik, Frankfurt am Main (DE)

(73) Assignee: PRO NATURA GESELLSCHAFT FÜR GESUNDE ERNÄHRUNG GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/946,772

(22) Filed: Nov. 19, 2015

(65) Prior Publication Data

US 2016/0175404 A1 Jun. 23, 2016

Related U.S. Application Data

(63) Continuation of application No. 12/094,648, filed as application No. PCT/EP2006/011231 on Nov. 23, 2006, now abandoned.

(60) Provisional application No. 60/757,413, filed on Jan. 10, 2006, provisional application No. 60/831,173, filed on Jul. 17, 2006.

(30) Foreign Application Priority Data

| | | |
|---|---|---|
| Nov. 23, 2005 | (DE) | 10 2005 056 170 |
| Dec. 16, 2005 | (DE) | 10 2005 060 767 |
| Dec. 20, 2005 | (DE) | 10 2005 061 330 |
| Dec. 30, 2005 | (DE) | 10 2005 063 194 |
| Jan. 5, 2006 | (DE) | 10 2006 001 016 |
| Mar. 22, 2006 | (DE) | 10 2006 013 623 |
| Mar. 27, 2006 | (DE) | 10 2006 014 420 |

(51) Int. Cl.
| | |
|---|---|
| A61K 38/44 | (2006.01) |
| A61K 38/52 | (2006.01) |
| A23P 10/30 | (2016.01) |
| A23L 33/20 | (2016.01) |
| A23L 33/10 | (2016.01) |
| A23L 33/00 | (2016.01) |

(52) U.S. Cl.
CPC ............ *A61K 38/443* (2013.01); *A23L 33/10* (2016.08); *A23L 33/20* (2016.08); *A23L 33/30* (2016.08); *A23P 10/30* (2016.08); *A61K 38/52* (2013.01); *C12Y 101/99011* (2013.01); *C12Y 503/01005* (2013.01); *A23V 2002/00* (2013.01); *C12Y 503/01018* (2013.01)

(58) Field of Classification Search
None
See application file for complete search history.

(56) References Cited

U.S. PATENT DOCUMENTS

| | | | | |
|---|---|---|---|---|
| 4,699,882 A * | 10/1987 | Visuri | ...................... | C12N 9/96 435/188 |
| 6,306,445 B1 * | 10/2001 | Xu | ......................... | A21D 2/267 426/18 |
| 8,460,911 B2 * | 6/2013 | Wyrobnik | ............ | A61K 9/4858 424/94.5 |
| 9,155,786 B2 * | 10/2015 | Wyrobnik | ............ | A61K 9/4858 |
| 9,415,093 B2 * | 8/2016 | Wyrobnik | .............. | A21D 8/042 |

OTHER PUBLICATIONS

Walcarius et al. J Material Chemistry, 15, p. 3663-3689, 2005.*
Falk et al. Direct electron transfer based enzymatic fuel cells. Electrochemical Acta, 2012, 82: 191-202.*

* cited by examiner

*Primary Examiner* — Iqbal H Chowdhury
(74) *Attorney, Agent, or Firm* — Heslin Rothenberg Farley & Mesiti P.C.

(57) ABSTRACT

There are disclosed compositions and methods for treating obesity using 5-D-fructose dehydrogenase. Other embodiments are also described.

20 Claims, No Drawings

AGENT FOR REDUCING THE USEABLE CALORIE CONTENT OF FOOD AND FOR THERAPEUTIC REDUCTION OF WEIGHT, IN PARTICULAR FOR USE IN THE CASE OF ADIPOSITY (OBESITY)

This application is a continuation of U.S. Ser. No. 13/681,366, filed Nov. 19, 2012, which is a continuation of U.S. Ser. No. 12/094,648, which is a 35 U.S.C. § 371 application of PCT/EP2006/011231, filed Nov. 23, 2006, and claims the benefit under 35 U.S.C. § 120 of said PCT application, and further claims the benefit under 35 U.S.C. § 119(e) of U.S. Provisional Patent Application Ser. No. 60/757,413, filed on Jan. 10, 2006 and U.S. Ser. No. 60/831,173, filed on Jul. 17, 2006. The contents of these applications are incorporated herein by reference.

The present invention relates to an agent for reducing the useable calorie content of food. The agent contains a compound that can effect the conversion of fructose to 5-keto-D-fructose. 5-keto-D-fructose cannot be metabolized by the human or animal body and is therefore significantly less caloric than fructose. The present invention also relates to an agent which, in addition to the first compound, contains a compound that can effect the conversion of glucose to fructose. According the invention the term "agent" includes a pharmaceutical composition, a medical device, a foodstuff and a special foodstuff.

According to the present invention, the terms "food" and "foodstuff" are used as synonyms. They mean to also include feed in the sense of animal feed. In the context of this application "special foodstuffs" are foodstuffs for particular nutritional uses, foods for special medical purposes, medical foods, food supplements, dietary supplements, dietetic food supplements, health foods, nutraceuticals, and food additives. In the context of this application the term foodstuff means to include special foodstuffs as used herein, where applicable.

Fructose is a ketohexose and is an important energy providing ingredient of food. It is present as a component of many di- and oligosaccharides, as free fructose or as both in numerous foodstuffs. In contrast to glucose, fructose is assimilated into the mucosa cells of the small intestine by eased carrier-mediated diffusion. The enzymatic degradation starts in the liver by the action of the adenosine triphosphate (ATP) dependent fructokinase, whereby fructose is converted to fructose 1-phosphate. In the liver and in the kidneys, fructose 1-phosphate is cleaved to glycerine aldehyde and dihydroxy acetone phosphate by aldolase B.

Food, e.g. fruits and fruit juices, contain a large amount of fructose, but in particular also sucrose, which is cleaved to fructose and glucose in the body. Over the past decades, there has been a dramatic increase in the consumption of free fructose (which is approx. 1.6-fold sweeter than glucose or sucrose) since the cheaper sweetener "high fructose corn syrup" (HFCS) was added to many of our beverages, bakery products and other sweet foodstuffs. Data from the USA show a parallel development between the sharp increase of obesity and the additives of free fructose. In contrast to glucose, fructose is metabolized independently of insulin. Since insulin influences the occurrence of the sensation of satiation indirectly, i.e. fructose does not eliminate the appetite, obesity may easily occur as a result of the extensive use of HFCS as a sweetener. Free fructose in large amounts may also favor hypertension. Large amounts of free fructose also influence the lipid profile (blood lipids) in an unfavorable way, since they promote the synthesis of lipids and thus increase the postprandial serum triglycerides. Patients with metabolic syndrome should not consume beverages that are sweetened with HFCS or sucrose. Fructose is also discussed as a cause of metabolic syndrome.

Thus, fructose is an important source of calories for the human body and must be given special consideration in all efforts to reduce the content of calories in the food. In the following, the term "fructose containing" refers to all substances and foodstuffs that either contain fructose in pure form or from which fructose can be released in the digestive tract. The fructose content of substances and foodstuffs refers to all the fructose in a fructose containing food or substance in whatever form (e.g. also as part of sucrose) it is contained in such a food or substance.

Departures from normal weight due to an increase in body weight, primarily in the proportion of fat, are referred to as adiposity (obesity), whereby, normally and in the sense of this invention, four grades are differentiated, namely grade 0=normal weight, grade I=overweight, grade II=adiposity and grade III=extreme adiposity. The individual grades are classified according to the well-known body mass index (BMI). An increase in fatty tissue and thus in body weight above a certain limit leads to an increase in various diseases, such as hypertension, and life expectancy decreases. The number of persons suffering from adiposity grade I to grade III has increased constantly in the industrialized countries over the past decades and amounts to 30 to 50% of the total population at present, depending on the statistic used and definition of the term overweight or obesity. For example, in the Federal Republic of Germany, every second person is overweight (adiposity grade I) and every sixth person has adiposity grade II or III. The number of adipose children is also increasing as a result of poor nutrition and lack of exercise. To date, therapy has been limited to nutrition therapy and, in extreme cases, surgical measures. It is a well-known fact that there is a very large and constantly increasing number of nutrition therapies and diets that generally do not result in lasting success. Even if there is an initial loss in weight, usually this results in the so-called yoyo effect, i.e. the sufferers initially lose weight, but put it back on again after the end or early termination of the diet. Often, in the end the body weight is even higher than prior to the beginning of the diet. Surgical measures, which are only used in particularly severe cases, have the aim of reducing the supply of nutrients or nutrient utilization, and are associated with high operation risks and long-term negative side effects. Nutrient deficits may thus result, due to impairments of absorption and insufficient supply with the food. These relate to vitamins, minerals and proteins. Up to one third of the surgical patients show a folic acid deficiency. In addition, iron, potassium, magnesium and vitamin A deficiencies may occur.

The drug therapies known to date for treating adiposity are controversial. Products have often had to be taken off the market due to severe side effects. All drugs that are still available today also have significant, unpleasant and frequent side effects, such as fatty stools, constipation and insomnia. A diet that reliably leads to a sustainable success and/or a broadly applicable therapy for adiposity in its different types without side effects is not known. Of course, the widespread use of surgical measures does not come into question. It remains to be said that those suffering from obesity and the specialists treating them are confronted by a quite hopeless and frustrating situation for all concerned.

An agent that does not have an effect on the body, but on the carbohydrates in the food and that would reduce the useable calorie content in the food would satisfy an extremely widespread and pressing need which has existed for decades. Such an agent would also overcome the prejudice widely held in the specialist world and among those suffering from obesity that a lasting weight reduction or the prevention of an increase in weight is not possible without suffering and without a significant change of nutrition habits. It would mean a dramatic improvement in the options available for the treatment of adiposity. Such an agent would also put an end to the as yet fruitless efforts of the specialist world to find an agent to treat adiposity which can be administered broadly, easily, and long-term, without causing side effects. This would apply all the more to an agent which, in addition, has no negative effects on health.

Thus, there is provided in accordance with embodiments of the present invention an agent that significantly reduces the useable calorie content of food, in particular for facilitating the intake of foodstuffs that normally contain fructose also in the case of adiposity, without resulting in an increase in weight. Further, there is provided in accordance with embodiments of the invention an agent to make it possible for persons suffering from adiposity to eat foodstuffs which until now were not allowed to them due to their fructose content or the eating of which was associated with negative effects for the sufferers' health. There is also provided in accordance with embodiments of the invention an agent that, after the intake of fructose, can reduce or prevent the associated negative effects on weight and/or health, in particular in the case of adiposity.

There is also provided, in accordance with embodiments of the invention an agent that can prevent persons who up to now have not suffered from adiposity from putting on weight as a result of eating fructose containing substances or foodstuffs. There is thus also provided in accordance with embodiments of the invention an agent to allow persons who are not suffering from adiposity to eat foodstuffs the intake of which would otherwise lead to the risk of weight gain, with the consequence that these persons might become adipose.

Therefore, the subject matter of the invention is an agent that contains 5-D-fructose dehydrogenase (syn. fructose 5-dehydrogenase). The agent according to the present invention brings about the conversion of fructose in the food into 5-keto-D-fructose by dehydrogenation. Thus, the fructose is changed in such a manner that it is no longer available to the metabolism of the human or animal body.

According to another aspect of the invention 5-D-fructose dehydrogenase is used, optionally in combination with glucose isomerase, for treatment of adiposity, for example in the form of a pharmaceutical composition. The treatment of adiposity may be therapeutic or prophylactic. Also, further diseases accompanying adiposity may be treated by making use of the agent according to the invention.

According to another aspect of the present invention, the agent is used for lowering the usable calorie content of food.

A subject matter of the invention is also an agent that reduces the bioavailability of fructose in the human or animal body with the help of a 5-D-fructose dehydrogenase.

A subject matter of the invention is also an agent that reduces the bioavailability of fructose and glucose in the human or animal body with the help of a 5-D-fructose dehydrogenase in combination with a glucose isomerase.

A subject matter of the invention is also an agent that reduces the content of fructose in a foodstuff with the help of a 5-D-fructose dehydrogenase.

A subject matter of the invention is also an agent that reduces the content of fructose and glucose in a foodstuff with the help of a 5-D-fructose dehydrogenase in combination with a glucose isomerase.

A subject matter of the present invention is further an agent for reducing the useable calorie content of food which contains a 5-D-fructose dehydrogenase—alone or in combination with a glucose isomerase.

The agent according to the invention is suited for the use in the case of adiposity and for the therapeutic or prophylactic treatment of adiposity, possibly accompanied by a further disease usually appearing together with adiposity, including diseases of the cardiovascular system (e.g. hypertension, coronary heart disease, venous insufficiency, heart failure, left-ventricular hypertrophy, arteriosclerosis), of metabolic and hormonal function (e.g. diabetes mellitus type II, dyslipidemias, hyperuricemia, hyperlipoproteinemia), of the respiratory system (e.g. sleep apnea, Pickwickian syndrome), of the hepatobiliary system (e.g. fatty liver, cholecystolithiasis), of the locomotor system (e.g. gonarthrosis, heel spur, arthrosis of the ankle joint), of the skin (e.g. intertrigo, hirsutism, striae) and for use in the case of neoplasias associated with adiposity (e.g. increased risk of endometrial, breast, cervical, gall bladder cancer, etc.), disorders of sexual function (e.g. reduced fertility, complications during birth), psychosocial problems (e.g. reduced self-confidence, social isolation, discrimination, problems with one's partner or at work), and other problems, such as reduced mobility and staying power, increased risk during operations and more difficult examination conditions.

All these diseases and health problems are often associated with adiposity.

A further subject matter of the invention is the use of a 5-D-fructose dehydrogenase—alone or in combination with a glucose isomerase—in the case of adiposity or in the case of health problems or diseases associated with adiposity (see above).

A further subject matter of the invention is the use of 5-D-fructose dehydrogenase—alone or in combination with a further enzyme, preferably together with glucose isomerase—for the manufacture of a medicament (pharmaceutical composition) for the prophylactic or therapeutic treatment of adiposity or diseases associated with adiposity (see above).

According to the present invention, a 5-D-fructose dehydrogenase—alone or in combination with a glucose isomerase—may also be used for reducing the useable calorie content in a foodstuff.

A 5-D-fructose dehydrogenase, in the context of this application, is an enzyme that can catalyze the dehydrogenation of fructose to 5-keto-D-fructose.

A possible method for the production of a 5-D-fructose dehydrogenase is, for example, described in Ameyama et al., Journal of Bacteriology 1981, 814-823, "D-Fructose Dehydrogenase of Gluconobacter industrius: Purification, Characterization and Application of Enzymatic Microdetermination of D-Fructose", the content of which is incorporated herein by reference.

The practical meaning of such an agent for the reduction of the useable calorie content of food becomes clearer if one considers that fructose is used very widely in the foodstuff industry as a sweetener. In the case of foodstuffs which contain sucrose, the content of calories can be reduced by about one half by the use of the agent according to the present invention which contains the enzyme 5-D-fructose dehydrogenase. During digestion, sucrose is enzymatically cleaved to glucose and fructose. The fructose fraction (50% of the calories contained in sucrose) is then dehydrogenated by said 5-D-fructose dehydrogenase to 5-keto-D-fructose and can therefore no longer be utilized by the body.

Glucose is the central carbohydrate of the energy and substrate metabolism. It is the basic component of many polysaccharides (e.g. starch). In the context of this application the term "glucose containing" refers to all substances and foodstuffs that either contain glucose in pure form or from which glucose can be released in the digestive tract. The glucose content of substances and foodstuffs refers to all the glucose in a glucose containing food or substance in whatever form (e.g. also as part of sucrose) it is contained in such a food or substance.

Therefore, a further reduction of the calorie content of food may be achieved according to the present invention by an agent that contains glucose isomerase as an additional active ingredient. The invention thus provides compositions and methods that can be used to enable sufferers of Adiposity to ingest fructose-containing foods or fructose- and glucose-containing foods A glucose isomerase in the context of this application is an enzyme that is able to transform glucose into fructose. This conversion can also be brought about, for example, by a xylose isomerase. Thus, such a xylose isomerase is, in the context of this application, also a glucose isomerase. A possible method for the production of a xylose isomerase is, for example, described in Yamanaka, Biochimica et Biophysika Acta, Volume 151 (3), 1968, 670-680, "Purification, Crystallization and Properties of the D-Xylose Isomerase from *Lactobacillus brevis*" and in Yamanaka, Methods in Enzymology, Volume 41, 1971, 466-471, "D-Xylose Isomerase from *Lactobacillus brevis*", the contents of which are incorporated herein by reference.

Such a combination agent can also be used in the form of two separate dose units, e.g. in two separate tablets, one of which contains glucose isomerase and the other 5-D-fructose dehydrogenase.

By combining 5-D-fructose dehydrogenase with the enzyme glucose isomerase, ingested glucose as well as the large amounts of glucose released by the degradation of carbohydrates are largely removed from the metabolism of calories by the body. Glucose isomerase has the property of converting glucose into fructose and vice versa with an equilibrium concentration of approximately 50% glucose and 50% fructose. Such an enzyme combination consisting of 5-D-fructose dehydrogenase and glucose isomerase is ideally suited for considerably reducing the calorie content of, for example starch containing food, such as potatoes. The glucose that is released from starch during digestion is transformed into fructose by said glucose isomerase, which is then converted by said 5-D-fructose dehydrogenase into 5-keto-D-fructose which is significantly less bioavailable. Thus, the 5-D-fructose dehydrogenase prevents the above described equilibrium from being established. Therefore, glucose isomerase will convert glucose into fructose, which itself will be dehydrogenated by the 5-D-fructose dehydrogenase to 5-keto-D-fructose, until no further glucose is present in the food and food pulp.

Also in the case of sucrose, an increased reduction of calories can be achieved with the combination agent. Fructose, which is released from sucrose during digestion, is converted into 5-keto-D-fructose by 5-D-fructose dehydrogenase, as described above. Therefore the glucose isomerase will attempt to re-establish the above described equilibrium by converting glucose into fructose. This conversion process continues until no further glucose is present in the food pulp. In this way, the content of calories of the sucrose containing dishes available to the body is reduced to a greater degree than if 5-D-fructose dehydrogenase is used on its own.

The combination agent according to the present invention thus leads to a large proportion of the glucose supplied to the body or released in the digestive tract being converted into fructose which in turn is converted into 5-keto-D-fructose, which is of much less value for the metabolism.

In a particularly easy way, the invention facilitates the transformation of fructose in a foodstuff into a form that prevents weight gain and enables weight loss. Thus, the invention also facilitates the intake of foodstuffs by persons who suffer from adiposity that had to be avoided by the sufferers up to now because of their content of fructose and glucose. Further, the invention allows the intake of fructose and glucose containing foodstuffs by persons who are not suffering from adiposity, without this leading to negative effects on their weight and/or health.

According to the present invention, 5-D-fructose dehydrogenase—alone or in combination with glucose isomerase—is further mentioned for use in medicine (first medical indication), for example as a pharmaceutical composition. Accordingly, a subject matter of the invention is also a product which consists of 5-D-fructose dehydrogenase—alone or in combination with glucose isomerase—or contains 5-D-fructose dehydrogenase—alone or in combination with glucose isomerase—beside one or more other active ingredients for use in a medical method, in particular in a method for the therapeutic treatment of the human or animal body. In the context of this application, a pharmaceutical composition is a product, in particular a substance or a substance mixture, for use in a method for surgical or therapeutic treatment of the human or animal body and in diagnostic methods that are performed on the human or animal body. Thus, in the context of this application, pharmaceutical compositions are also products, in particular substances or substance mixtures, that are meant or suitable for curing, alleviating, preventing or determining adiposity.

The term "treating" when used in connection with the foregoing disorders includes amelioration, prevention or relief from the symptoms and/or effects associated with these disorders and includes the prophylactic administration of an enzyme or a mixture thereof to diminish the likelihood or seriousness of the conditions.

According to a further aspect of the present invention, a foodstuff is provided which contains 5-D-fructose dehydrogenase—alone or in combination—with glucose isomerase. Further, according to the present invention, a foodstuff is provided which contains 5-D-fructose dehydrogenase—alone or in combination with glucose isomerase—in an amount which is sufficient to convert fructose into 5-keto-D-fructose and which, in addition, contains glucose isomerase in an amount which is effective for transforming glucose into fructose. Such a foodstuff may be produced using a method for treating a foodstuff in which the foodstuff is placed in contact with a 5-D-fructose dehydrogenase—alone or in combination with glucose isomerase—under such conditions under which the 5-D-fructose dehydrogenase can dehydrogenate fructose to 5-keto-D-fructose and under which the glucose isomerase can convert glucose into fructose. In contrast to otherwise untreated foodstuffs, such a foodstuff has a reduced content of fructose or, if the agent contains both enzymes, a reduced content of fructose and glucose, and therefore, for the first time, is suitable to be consumed by persons who want to control their weight, including adipose persons. Furthermore, a foodstuff can be prepared by a method in which a 5-D-fructose dehydrogenase is added to the foodstuff—alone or in combination with glucose isomerase—in a manner in which the action of the enzyme or both enzymes only starts after the intake of the foodstuff. Such a foodstuff that contains 5-D-fructose dehydrogenase or 5-D-fructose dehydrogenase and glucose isomerase has the same taste as an untreated foodstuff and is, for the first time, suitable to be consumed by persons who want to control their weight including adipose persons due to the reduced content of fructose or fructose and glucose which is established after eating.

According to a further aspect, according to the present invention, 5-D-fructose dehydrogenase—alone or in combination with glucose isomerase—is provided as a medical device. The subject matter of the invention is accordingly also a medical device that consists of 5-D-fructose dehydrogenase—alone or in combination with glucose isomerase—or contains the 5-D-fructose dehydrogenase—alone or in combination with glucose isomerase—beside one or more other active ingredients.

In the following, the invention will be described further in its various aspects.

5-D-Fructose dehydrogenase is a compound that has been known for nearly 40 years, but has only been used for analytical purposes to date. Glucose isomerase is a compound that has been known for more than 40 years and has only been used for starch saccharification to date. In the industry, it is used for the conversion of glucose into fructose as well as for the conversion of fructose into glucose.

5-D-fructose dehydrogenase, in particular in combination with glucose isomerase, has not been used in the medical/pharmaceutical field to date, in particular not in adiposity in humans or animals. Thus, the invention discloses the first medical indication for 5-D-fructose dehydrogenase and the first medical indication for the combination of the two enzymes. Until now, the two enzymes have not been used for the therapeutic treatment of the human or animal body or for diagnostic purposes on the human or animal body.

The agent according to the present invention may be taken orally prior to meals, immediately before meals, with meals or immediately after meals, so that it can exert its dehydrogenating effect on fructose and optionally converting effect on glucose in the food pulp. The agent according to the present invention may contain the enzyme(s) without further additives. However, it is preferable that the agent according to the present invention further contains additives that are pharmaceutically acceptable and/or acceptable for foodstuffs, such as for example extenders, binders, stabilizers, preservatives, flavourings, etc. Such additives are commonly used and well known for the production of pharmaceutical compositions, medical devices, foodstuffs, and special foodstuffs and the person skilled in the art knows which additives in which amounts are suitable for certain presentation forms. The agents according to the present invention may for example contain as additives dicalcium phosphate, lactose, modified starch, microcrystalline cellulose, maltodextrin and/or fibersol.

The agents according to the present invention can also be added to a foodstuff before eating. They may even be added to the foodstuff at the production stage, with the aim of developing their effect only after consuming the foodstuff. This may be achieved by microencapsulation, for example. With this, the useable fructose and/or glucose content of the foodstuff may be reduced, without negatively affecting its taste. Therefore, preparations are particularly useful that contain 5-D-fructose dehydrogenase—alone or in combination with glucose isomerase—and which release these enzymes only in the digestive tract of a human or animal or let them become effective in another way, in particular in the stomach or small intestine. Therefore, the invention can be used for example in the production of sweets, fruit preparations (e.g. apple sauce), jam, honey, chocolate and chocolate products, bakery products (e.g. biscuits and cakes), breads, pastas, vegetable dishes, potato dishes, ice cream, cereals, dairy products (e.g. fruit yogurt and pudding), fructose- and/or glucose-containing beverages, fructose- and/or glucose-containing sauces (e.g. tomato ketchup) and fructose- and/or glucose-containing sweeteners. For dishes that are boiled or baked, the agents according to the present invention could e.g. be mixed into or sprinkled onto them after cooling.

Since fructose is widely used as a sweetener in foodstuffs that are especially produced for diabetics, the addition of the agents according to the present invention to diabetic food before eating or the addition of the agents according to the present invention during the production of diabetic food allows diabetics who suffer from adiposity to eat diabetic food, such as the above mentioned foodstuffs in their respective form as diabetic foods.

The agent according to the present invention may also be added to a foodstuff, to exert its effect on the fructose originating from another foodstuff and in the case of an agent containing both enzymes also on the glucose originating from another foodstuff after their consumption. An example of this would be the addition of the agent according to the present invention to a spread so that the reduction of the calories that are contained in the bread and that can be utilized by the body occurs after the intake of the bread, without an impairment of taste of the bread. Another example would be mixed spices and mayonnaise, among other things for use with french fries.

5-D-fructose dehydrogenase and the combination agent may also be used in immobilized form. This is useful for the treatment of liquid foodstuffs. For example, 5-D-fructose dehydrogenase can be embedded in a matrix which is permeable for fructose. If a fructose containing liquid foodstuff is allowed to flow along the enzyme containing matrix, then fructose is extracted from the foodstuff by the action of the enzyme and converted into 5-keto-D-fructose.

A subject matter of the present invention are also agents that in addition to other active ingredients also contain 5-D-fructose dehydrogenase, either alone or in combination with glucose isomerase.

The agent may be formulated in any form which is suitable for the intended route of administration. A preferred route of administration is oral administration. For oral administration, the agent may be formulated for example in the form of capsules (coated or non-coated) containing powder, coated or non-coated pellets, granules or micro-/mini-tablets or in the form of tablets (coated or non-coated) pressed from powder, coated or non-coated pellets, dragées or micro-/mini-tablets. The agent may also be formulated for example in the form of gel caps or in liquid form as solution, drops, suspension or gel. The agent may also be formulated e.g. as dried or moist oral supplement. The formulation of the agent according to the present invention as powder is particularly suitable for admixing with foodstuff. The powder may be sprinkled onto a meal or mixed into a pulp or beverage. It is particularly beneficial, if the agent offered as bulk powder is packaged in single dosage amounts, such as in single bags or capsules, or if it is provided in a dosing dispenser.

For oral administration, the 5-D-fructose dehydrogenase—alone or in combination with glucose isomerase—may be used with acceptable excipients and/or carriers.

The total amount of the carrier and/or excipient of an agent containing 5-D-fructose dehydrogenase or 5-D-fructose dehydrogenase and glucose isomerase is preferably between 5 and 99.9% by weight, more preferably between 10 and 80% by weight and even more preferably between 25 and 60% by weight of the composition.

Suitable excipients and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethyl cellulose, corn starch, modified starch, fibersol, gelatine, hydroxypropylmethyl cellulose and the like (including mixtures thereof).

Preferable carriers include calcium carbonate, magnesium stearate, maltodextrin, dicalcium phosphate, modified starch, microcrystalline cellulose, fibersol, gelatine, hydroxypropylmethyl cellulose and mixtures thereof.

The various ingredients and the excipient and/or carrier may be mixed and formed into the desired form using common methods well known to the skilled person. The administration form according to the present invention which is suited for the oral route, such as e.g. tablet or capsule, may be coated with a coating which is resistant against low pH values (approximately pH 1 to 2.5) and which dissolves at a pH value of approximately 3.0 to 8.0, preferably at a pH value of 3.0 to 6.5 and particularly preferable at a pH value of 4.0 to 6.0. An optionally used coating should be in accordance with the pH optimum of the enzyme used and its stability at pH values to which the formulation will be exposed. Also a coating may be used which is not resistant to low pH values but which delays the release of the enzyme at low pH values. It is also possible to prepare the agent according to the present invention as coated (see above) pellets, granules or micro-/mini-tablets which can be filled into coated or non-coated capsules or which can be pressed into coated or non-coated tablets. Suitable coatings are, for example, cellulose acetate phthalate, cellulose derivates, shellac, polyvinylpyrrolidone derivates, acrylic acid, polyacrylic acid derivatives and polymethyl methacrylate (PMMA), such as e.g. Eudragit® (from Röhm GmbH, Darmstadt, Germany), in particular Eudragit® L30D-55. The coating Eudragit® L30D-55 is dissolved, for example, at a pH value of 5.5 and higher. If it is desired to release the enzyme already at a lower pH value, this may be achieved e.g. by the addition of sodium hydroxide solution to the coating agent Eudragit® L30D-55, because in this case carboxyl groups of the methacrylate would be neutralised. Therefore, this coating will be dissolved, for example, already at a pH value of 4.0 provided that 5% of the carboxyl groups are neutralised. The addition of about 100 g of 4% sodium hydroxide solution to 1 kg of Eudragit® L30D-55 would result in a neutralisation of about 6% of the carboxyl groups. Further details about formulation methods and administration methods can be found in the 21st edition of "Remington: The Science & Practice of Pharmacy", published 2005 by Lippincott, Williams & Wilkins, Baltimore, USA, in the Encyclopedia of Pharmaceutical Technology (Editor James Swarbrick) and in Prof. Bauer "Lehrbuch der Pharmazeutischen Technologie", 18th edition, published 2006 by Wissenschaftliche Verlagsgesellschaft (ISBN 3804-72222-9). The contents of these documents are incorporated herein by reference.

Other suitable acceptable carriers or adjuvants for use in the present invention include, but are not restricted to water, mineral oil, ethylene glycol, propylene glycol, lanolin, glyceryl stearate, sorbitan stearate, isopropyl myristate, isopropyl palmitate, acetone, glycerine, phosphatidylcholine, sodium cholate or ethanol.

The compositions for use in the present invention may also comprise at least one coemulsifying agent which includes but is not limited to oxyethylenated sorbitan monostearate, fatty alcohols, such as stearyl alcohol or cetyl alcohol, or esters of fatty acids and polyols, such as glyceryl stearate.

The agents according to the present invention may be provided in a stabilized form. Generally, stabilization methods and procedures which may be used according to the present invention include any and all methods for the stabilization of chemical or biological material which are known in the art, comprising e.g. the addition of chemical agents, methods which are based on temperature modulation, methods which are based on irradiation or combinations thereof. Chemical agents that may be used according to the present invention include, among others, preservatives, acids, bases, salts, antioxidants, viscosity enhancers, emulsifying agents, gelatinizers, and mixtures thereof.

Usually, the industrial production of enzymes is performed in a technical fermentation way using suitable microorganisms (bacteria, moulds, fungi). Usually the strains are recovered from natural ecosystems according to a special screening protocol, isolated as pure cultures as well as improved in their properties with respect to the enzyme spectrum and biosynthesis performance (volume/time yield). Enzyme production may also be carried out by methods developed in the future.

5-D-fructose dehydrogenase is commercially available (e.g. Sigma-Aldrich or Toyobo Enzymes, Japan) and is usually prepared in a microbiological way with the help of the microorganism Gluconobacter industrius. Glucose isomerase is also commercially available (e.g. Sigma-Aldrich or Novozymes A/S, Denmark) and usually prepared in a microbiological way with the help of the microorganism *Streptomyces murinus*. However, the invention is not limited to the enzymes that are commercially available at the moment, but generally relates to enzymes that can catalyze the conversion of fructose—specifically or non-specifically—to 5-keto-D-fructose, and of glucose—specifically or non-specifically—to fructose. A person skilled in the art can prepare suitable further enzymes by conventional methods, for example by mutagenesis of the gene encoding 5-D-fructose dehydrogenase which is present in Gluconobacter industrius or by mutagenesis of the gene encoding glucose isomerase in *Streptomyces murinus*. The enzymes may also be prepared with the help of other microorganisms, such as fungi, in sufficient amounts and the required purities, also by the use of the genetic engineering methods which are presently known or may be developed in the future. For example, if it is desired to produce the enzymes with other microorganisms, then the genetic information of a microorganism which has been found initially by extensive screening and which has been proven to be a suitable source of the enzyme with the desired properties can be transferred to a microorganism which is normally used for the production of enzymes. Also the modification of the enzyme(s) and the production of the enzyme(s) by means of methods which are presently known or may be developed in the future in the area of industrial enzyme development and enzyme production, such as genetic engineering, is possible. The use and the manner of performing all these methods for developing and producing the enzyme(s) with the desired purities and activities and with the desired properties, in particular with respect to the stability of the enzyme(s) at various pH values, regarding the optimum of the pH value, the stability at various temperatures and temperature optimum, are well known to a person skilled in the art. The explanations in chapter 2 (page 82 to page 130) of the textbook "Lebensmittel-Biotechnologie and Ernährung" of Heinz Ruttloff, Jürgen Proll and Andreas Leuchten-berger, published by Springer Verlag 1997 (ISBN 3-540-61135-5) describe these methods in detail. These methods are also described in "Advances in Fungal Biotechnology for Industry, Agriculture, and Medicine" by Jan S. Tkacz, Lene Langeand (published in 2004, ISBN 0-306-47866-8), in "Enzymes in Industry: Production and Applications" by Wolfgang Aehle (Editor), published in 2004, ISBN 3527295925 and in "Microbial Enzymes and Biotransformations" by Jose-Luis Barredo (Humana Press 2005, ISBN 1588292533). These documents are herewith incorporated into the patent application by reference. All this also applies to the enzymes mentioned below that can optionally be added to the agent according to the present invention.

The activity of 5-D-fructose dehydrogenase is defined in units (assay available e.g. from Sigma-Aldrich), whereby one unit is the amount of 5-D-fructose dehydrogenase that converts one micromole of D-fructose to 5-keto-D-fructose per minute at pH 4.5 and 37° C. Generally, the activity of 5-D-fructose dehydrogenase per dose unit should be between 10 and 5 million units, preferably between 25 and 2.5 million units and particularly preferably between 50 and 1 million units.

In the case of the combination agent according to the present invention which also contains glucose isomerase, the composition should contain glucose isomerase in an amount of 0.01 to 100,000 GIU, preferably of 0.05 to 10,000 GIU and particularly preferably of 0.1 to 1,000 GIU per dose unit. One unit of this enzyme is defined as a glucose isomerase unit (GIU). One GIU converts 1 g of glucose into fructose at a pH value of 6.0 and at a temperature of 37° C. from a solution of initially 10% (percent by weight, i.e. 10 g of glucose+90 g of water) in 5 minutes.

The wide range of the above mentioned dosages may be explained by the fact that the agent according to the present invention can be applied for many uses, such as the different categories of adiposity and its accompanying and resulting diseases, or simply the effort of persons of normal weight to limit the intake of calories for preventing weight gain. Furthermore, the different dosages also result from the fact that strongly varying amounts of fructose and glucose are administered to the body, depending on the respective food.

The agent according to the present invention may comprise one or more additional enzymes, such as invertase (syn. beta-fructofuranosidase or beta-fructosidase), lactase (syn. beta-galactosidase), maltase (syn. alpha-glucosidase), alpha-amylase, beta-amylase, glucoamylase, pullulanase, isoamylase, amyloglucosidase, cyclomaltodextrin glucantransferase (CGTase). These enzymes have the property of releasing fructose and/or glucose from fructose and/or glucose containing substances and foodstuffs—alone or in combination with one or more of these enzymes—, whereby the enzymes pullulanase and isoamylase also increase the efficiency of glucoamylase and beta-amylase. All these enzymes are commercially available (e.g. BioCat Inc., Troy, USA or Novozymes A/S, Denmark or Amano Enzymes Inc., Japan or Sigma-Aldrich) and, up to now, have never been used in combination with 5-D-fructose dehydrogenase—alone or in combination with glucose isomerase—in the medical/pharmaceutical field, in particular not in the case of adiposity. Thus this application discloses the first medical indication for 5-D-fructose dehydrogenase—alone or in combination with glucose isomerase—in combination with any or all of these enzymes. Examples for agents according to the present invention include:

5-D-fructose dehydrogenase in combination with invertase, or 5-D-fructose dehydrogenase in combination with glucose isomerase and invertase, or 5-D-fructose dehydrogenase in combination with glucose isomerase and lactase and invertase, still further 5-D-fructose dehydrogenase in combination with glucose isomerase, Invertase, alpha amylase, beta amylase, glucoamylase, maltase, iso-amylase and pullulanase (combination of 9 enzymes), or 5-D-fructose dehydrogenase in combination with glucose isomerase, alpha amylase, beta amylase, glucoamylase, maltase, iso-amylase and pullulanase as well as invertase and lactase (combination of 10 enzymes).

For example, said invertase can release glucose and fructose from e.g. sucrose and said lactase can release glucose from lactose. Beta-amylase breaks down e.g. 1,4-alpha bonds in starch, starting at the non-reducing end of the polysaccharide chain with cleaving of maltose, and glucose is released by the action of maltase on maltose. By the addition of one or more of these enzymes to the agent according to the present invention, the endogenic release of fructose and/or glucose from fructose- and/or glucose-containing substances or foodstuffs, in particular from sucrose and starch, may also be promoted and accelerated, so that the conversion of fructose into 5-keto-D-fructose which is catalyzed by 5-D-fructose dehydrogenase and/or the conversion of glucose to fructose, which is effected by glucose isomerase, may occur earlier. Therefore, the addition of one or more of these enzymes to the agent according to the present invention may have the benefit of reducing the required amount of 5-D-fructose dehydrogenase and glucose isomerase.

The activity of invertase is measured in Sumner units (SU, assay available e.g. from BioCat Inc., Troy, Va., USA). An SU is defined as the amount of the enzyme which converts 1 mg of sucrose into glucose and fructose under standard test conditions within 5 minutes at 20° C. and a pH value of 4.5. If the agent according to the present invention also contains invertase, the activity of the invertase per dose unit should be between 50 and 250,000 SU, preferably between 100 and 150,000 SU and particularly preferably between 150 and 100,000 SU per dose unit.

The activity of lactase is given in Food Chemical Codex (FCC) units (assay is published in the Food Chemical Codex, fifth edition, and also available e.g. from Bio Cat Inc. Troy, Va. or Amano Enzymes, Japan or from Sigma Aldrich). If the agent according to the present invention also contains lactase, the activity of the lactase per dose unit should be between 50 and 200,000 FCC units, preferably between 100 and 100,000 FFC units and particularly preferably between 150 and 50,000 FCC units.

The activity of maltase is defined in units, wherein one unit is the amount of maltase which will convert maltose to D-glucose at a rate of one milligram per minute at 37° C. and a pH of 4.0 in a 10% maltose solution by weight.

Where the agent according to the present invention also contains maltase, the activity per dose unit should be between 100 and 100,000 units, preferably between 200 and 50,000 units and particularly preferably between 500 and 20,000 units.

Also for the other enzymes mentioned, the standard test conditions and the way in which the enzyme activities are to be determined are known and can be read up by specialists in the field.

Insofar as one or more of the optional enzymes are added to the agent according to the present invention, they—as is the case for the 5-D-fructose dehydrogenase and the glucose isomerase—should be used in sufficient amounts so that they can develop a sufficient enzyme activity for the intended purpose, e.g. sufficient invertase, so that an amount of sucrose usually ingested with a normal meal (e.g. 15 g) can be cleaved, and/or lactase, so that an amount of lactose usually ingested with a normal meal (e.g. 10 g) can be cleaved.

The enzymes used can be for example in solid form, e.g. as crystalline or amorphous granules or powders, as a paste or as a liquid, as well as in other forms. In some embodiments, the enzyme is a free enzyme. In other embodiments, the enzyme may e.g. be immobilized on substrate, which can be powderized if necessary before the enzyme is used in accordance with the invention.

If the agent according to the present invention is added to a foodstuff before eating or during production, the activity of 5-D-fructose dehydrogenase should be between 10 and 250,000 units, preferably between 25 and 150,000 units and particularly preferably between 50 and 100,000 units per gram fructose in the foodstuff. If the agent also contains glucose isomerase and the agent according to the present invention is added to a foodstuff before eating or during production, the activity of glucose isomerase should be between 0.01 and 20,000 units, preferably between 0.05 and 10,000 units and particularly preferably between 0.1 and 1000 units per gram glucose in the foodstuff.

If the agent according to the present invention is added to a foodstuff before eating or during production and if the agent contains 5-D-fructose dehydrogenase and glucose isomerase, the activity of 5-D-fructose dehydrogenase should be between 10 and 250,000 units, preferably between 25 and 150,000 units and particularly preferably between 50 and 100,000 units per gram of fructose and glucose combined contained in the foodstuff.

It may be advantageous to add an electron acceptor to the agent according to the present invention at e.g. a ratio (acceptor:substrate) of 1:1 to 1:1,000, preferably at a ratio of 1:2 to 1:200, particularly preferably at a ratio of 1:10 to 1:50. Examples of suitable acceptors which may be used include $NAD^+$, $NADP^+$, $FAD^+$, vitamins, such as vitamin C, vitamin E or vitamin A, ferricyanide, ketones, aldehydes, 2,6-dichlorophenolindophenol, phenazine methosulfate, nitroblue tetrazolium (including mixtures thereof), but are not limited thereto.

The physiologically present electrolytes should be sufficient for the function of the glucose isomerase. But it may also be advantageous to add electrolytes to the agent according to the present invention, e.g. in an amount of 0.0001% to 0.1% of the substrate (glucose). Examples of the electrolytes include, but are not limited to, $MgSO_4$, $Na_2CO_3$, $NaHCO_3$, $NaOH$, $Na_2SO_4$, $MgCO_3$, $H_2SO_4$, $NaS_2O_3$, $NaS_2O_5$ (including mixtures thereof).

It may also be advantageous to add metal ions, in particular cations, such as $Mn^{2+}$, $Mg^{2+}$, $Ca^{2+}$, $Zn^{2+}$, $Fe^{2+}$, $Co^{2+}$ or $Cu^{2+}$, including mixtures thereof, to the agent according to the present invention, namely preferably in a molar ratio of $10^{-6}$ to $10^{-2}$. For the above mentioned (xylose) glucose isomerase which is described by Yamanaka, in particular $Mn^{2+}$ is a suitable cation.

Capsule sizes mentioned below refer to the size definitions used by Capsugel Belgium BVBA, Bornem, Belgium. The size of the capsules should be chosen according to the specific formulation of the agent.

A composition according to the present invention for the production of capsules (for example of size 00) may consist of 370 mg of 5-D-fructose dehydrogenase with an activity of 90 units/mg and 100 mg of dicalcium phosphate per capsule.

Another example for a dosage form according to the present invention consists of capsules (size 1) that contain 110 mg of 5-D-fructose dehydrogenase with an activity of 500 units/mg as well as 50 mg of invertase with an activity of 200 SU units/mg as well as 50 mg of maltase with an activity of 200 units/mg and 90 mg of maltodextrin.

Another example for the dosage form according to the present invention consists of capsules of size 00 which contain 200 mg of 5-D-fructose dehydrogenase with an activity of 500 units/mg as well as 100 mg of invertase with an activity of 200 SU units/mg as well as 150 mg of dicalcium phosphate.

In the case of a combination agent in which 5-D-fructose dehydrogenase and glucose isomerase are used, a capsule of size 0 may contain 250 mg of 5-D-fructose dehydrogenase with an activity of 90 units/mg and 20 mg of glucose isomerase with an activity of 1 GIU/mg and 50 mg dicalcium phosphate.

A further example of a combination preparation with 5-D-fructose dehydrogenase and glucose isomerase for the production of capsules of size 00 may contain 370 mg of 5-D-fructose dehydrogenase with an activity of 90 units/mg, 30 mg of glucose isomerase with an activity of 1 GIU/mg and 70 mg of dicalcium phosphate.

A further example of a combination preparation with 5-D-fructose dehydrogenase and glucose isomerase for the production of capsules of size 00 may contain 110 mg of 5-D-fructose dehydrogenase with an activity of 500 units/g, 50 mg of glucose isomerase with an activity of 1 GIU/mg, 100 mg of invertase with an activity of 200 SU units/mg, 90 mg of lactase with an activity of 100 FCC units/mg and 120 mg of dicalcium phosphate.

A further example of a combination preparation with 5-D-fructose dehydrogenase and glucose isomerase for the production of capsules (e.g. of size 3) may consist of 55 mg of 5-D-fructose dehydrogenase with an activity of 1000 units/mg, 50 mg of glucose isomerase with an activity 1 GIU/mg and 55 mg of dicalcium phosphate per capsule.

A further example for a dosage form according to the present invention consists of capsules (size 00) that contain 165 mg of 5-D-Fructose dehydrogenase with an activity of 1000 units/mg, 150 mg of glucose isomerase with an activity of 1 GIU/mg and 155 mg of dicalcium phosphate per capsule.

The invention may for example contain between 10 and 5 million units of 5-D-fructose dehydrogenase per dose unit. In addition, suitable additives in the required amount may be used. The invention may, in addition, contain glucose isomerase, for example between 0.01 and 100,000 GIU (=glucose isomerase units) per dose unit.

The invention may be provided for medical purposes and non-medical purposes, e.g. as a pharmaceutical composition, medical device, foodstuff or special foodstuff.

With the agents according to the present invention the content of calories of carbohydrate containing food that can be utilized by the body can be reduced to such a degree that a marked weight loss can be achieved or a weight gain can be prevented despite the intake of carbohydrate rich food. The agents according to the present invention are thus suitable for use in methods for the therapeutic treatment of the human or animal body in which a limitation or reduction of the intake of food calories originating from carbohydrates is intended, e.g. in the case of the therapy of diseases of the cardiovascular system (e.g. hypertension, coronary heart disease, venous insufficiency, heart failure, left-ventricular hypertrophy, arteriosclerosis), of metabolic and hormonal function (e.g. diabetes mellitus type II, dyslipidemias, hyperuricemia, hyperlipoproteinemia), of the respiratory system (e.g. sleep apnea, Pickwickian syndrome), of the hepatobiliary system (e.g. fatty liver, cholecystolithiasis), of the locomotor system (e.g. gonarthrosis, heel spur, arthrosis of the ankle joint), of the skin (e.g. intertrigo, hirsutism, striae), in the therapy of neoplasias (e.g. increased risk of endometrial, breast, cervical, gall bladder cancer, etc.), in the therapy of disorders of sexual function (e.g. reduced fertility, complications during birth), in the therapy of psychosocial problems (e.g. reduced self-confidence, social isolation, discrimination, problems with one's partner or at work) and other problems, such as reduced mobility and staying power, increased risk during operations and more difficult examination conditions. All these diseases and health problems are often associated with adiposity.

The agents according to the present invention are in particular suitable for use in the case of adiposity and for the therapeutic treatment of adiposity.

In the description and following claims, the term "fructose equivalent-containing" refers to all substances and foodstuffs that contain fructose (a) as fructose per se, (b) in a form from which fructose can be released in the digestive tract (e.g. by cleavage as fructose from a saccharide chain containing at least two saccharide monomers), (c) in a form that can be converted to fructose, e.g. as glucose per se, or (d) in a form that can be released in the digestive tract and converted to fructose, e.g. as a saccharide chain containing at least two saccharide monomers, at least one of which can be cleaved from the saccharide chain as glucose.

In the description and following claims, the term "total fructose" refers to the total content of fructose in a foodstuff (a) as fructose per se, (b) in a form from which fructose can be released in the digestive tract (e.g. by cleavage as fructose from a saccharide chain containing at least two saccharide monomers), (c) in a form that can be converted to fructose, e.g. as glucose per se, or (d) in a form that can be released in the digestive tract and converted to fructose, e.g. a saccharide chain containing at least two saccharide monomers, at least one of which can be cleaved from the saccharide chain as glucose.

In the description and following claims, the term "effective fructose content" of an item refers to the effective amount of total fructose in that item, taking into account the prior action of fructose converting enzymes that have been added to the item or the future action of fructose converting enzymes that have been added to the item. Thus, for example, a foodstuff having a given fructose content and having microencapsulated 5-D-fructose dehydrogenase incorporated therein will have a lower effective fructose content than a foodstuff which lacks the microencapsulated 5-D-fructose dehydrogenase but is otherwise identical, since release of the 5-D-fructose dehydrogenase after ingestion will result in at least a portion of the fructose in the foodstuff being converted to 5-keto D-fructose.

Thus, there is provided, in accordance with embodiments of the invention, a 5-D-fructose dehydrogenase, optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase, for use in medicine.

There is also provided, in accordance with embodiments of the invention, a pharmaceutical composition comprising 5-D-fructose dehydrogenase optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase.

In some embodiments, at least one of the enzymes, or the pharmaceutical composition, is protected by a coating to be stable at pH values of less than 4, preferably less than 3. In some embodiments, the composition of matter as described above is in a form for oral administration. In some embodiments, the composition of matter as described above is in a form suited to be added to food at the production stage of the same and/or before eating.

There is also provided, in accordance with embodiments of the invention, a medical device comprising 5-D-fructose dehydrogenase optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase. In some embodiments, the medical device includes one or more enzyme(s) protected by a coating to be stable at pH values of less than 4, preferably less than 3. In some embodiments, the medical device is in a form for oral administration. In some embodiments, the medical device is in a form suited to be added to food at the production stage of the same and/or before eating.

There is also provided, in accordance with embodiments of the invention, a foodstuff comprising 5-D-fructose dehydrogenase in combination with invertase and/or maltase and/or lactase.

There is also provided, in accordance with embodiments of the invention, a special foodstuff comprising 5-D-fructose dehydrogenase optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase. In some embodiments, the special foodstuff includes one or more enzyme(s) protected by a coating to be stable at pH values of less than 4, preferably less than 3. In some embodiments, the special foodstuff is in a form for oral administration. In some embodiments, the special foodstuff according is in a form suited to be added to food at the production stage of the same and/or before eating.

In some embodiments, the pharmaceutical composition, medical device or the special foodstuff as described above comprises 5-D-fructose dehydrogenase in combination with glucose isomerase.

There is also provided, in accordance with embodiments of the invention, the use of 5-D-fructose dehydrogenase, optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase, for the production of an agent, preferably a pharmaceutical composition, for the curative or prophylactic treatment of adiposity. In some embodiments, the adiposity is accompanied by disturbances of the cardiovascular system and/or of the metabolic and hormone based function and/or of the respiratory system and/or of the hepatobiliary system and/or disturbances of the locomotor system and/or diseases of the skin and/or neoplasias and/or disorders of the sexual function and/or psychosocial problems and/or reduced mobility and staying power and/or an increased operation risk and/or more difficult examination conditions. In some embodiments, the disturbances of the cardiovascular system are hypertension, coronary heart disease, venous insufficiency, heart failure, left-ventricular hypertrophy and/or arteriosclerosis. In some embodiments, the disturbances of the metabolic or hormonal function are diabetes mellitus type II, dyslipidemias, hyperuricemia and/or hyperlipoproteinemia. In some embodiments, the disturbances of the respiratory system are sleep apnea and/or the Pickwickan syndrome. In some embodiments, the disturbances of the hepatobiliary system are fatty liver and/or cholecystolithiasis. In some embodiments, the disturbances of the locomotor system are gonarthrosis, heel spur and/or arthrosis of the ankle joint. In some embodiments, the disturbances of the skin are intertrigo, hirsutism and/or striae. In some embodiments, the neoplasias are endometrial, mama, cervix and/or gall bladder carcinoma. In some embodiments, the disorders of the sexual function are reduced fertility and/or an increased risk of complications in the case of birth. In some embodiments, the psychosocial problems are reduced self-confidence, social isolation, discrimination and/or, problems with the partner and/or at the job.

There is also provided, in accordance with embodiments of the invention, the use of 5-D-fructose dehydrogenase, optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase for production of an agent, preferably a pharmaceutical composition, for lowering the bioavailability of fructose and/or glucose in the human or animal body.

There is also provided, in accordance with embodiments of the invention, the use of 5-D-fructose dehydrogenase, optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase for production of an agent, preferably a pharmaceutical composition, for lowering the content of fructose and/or glucose in a foodstuff.

There is also provided, in accordance with embodiments of the invention, the use of 5-D-fructose dehydrogenase, optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase for production of an agent, preferably a pharmaceutical composition, for lowering the usable calorie content of food.

In some embodiments, in the use described above, the agent, preferably the pharmaceutical composition, is in a form for oral administration.

In some embodiments, in the use described above, at least two enzymes are present. In some embodiments, the two enzymes are 5-D-fructose dehydrogenase and glucose isomerase.

In some embodiments, in the use described above, the agent is selected from a pharmaceutical composition, a medical device, a foodstuff or a special foodstuff.

In some embodiments, in the use described above, the enzymes are protected by a coating to be stable at pH values of less than 4, preferably less than 3.

In some embodiments, in the use described above, the agent is in a form for oral use.

In some embodiments, in the use described above, the product is suited to be added to food at the production stage of the same and/or before eating.

In some embodiments, in the use described above, the product is in a form for use in immobilised form.

There is also provided, in accordance with embodiments of the invention, a process for the treatment of a foodstuff, comprising the steps of contacting the foodstuff with a 5-D-fructose dehydrogenase optionally in combination with one or more enzyme(s) selected from glucose isomerase, invertase, lactase, maltase, alpha-amylase, beta-amylase, glucoamylase, pullulanase, isoamylase, amyloglucosidase and cyclomaltodextrin glucanotransferase, and initiating the reduction of the fructose content and optionally the reduction of the glucose content of the foodstuff. In some embodiments, as a further step prior to the initiation, ingestion of the foodstuff takes place.

There is also provided, in accordance with embodiments of the invention, a mammalian-ingestible composition of matter which comprises an enzyme that converts D-fructose into a form that is biologically inactive in a chosen mammalian body or a mixture of such enzymes.

There is also provided, in accordance with embodiments of the invention, a mammalian-ingestible composition of matter which comprises an enzyme that converts D-fructose into a form that cannot be digested in a chosen mammalian digestive tract.

There is also provided, in accordance with embodiments of the invention, a mammalian-ingestible composition of matter which comprises an enzyme that converts D-fructose into a form that is not metabolizable in a chosen mammalian body.

In some embodiments, the chosen mammalian body is a human body. In some embodiments, the chosen mammalian body is a non-human body. In some embodiments, the form into which D-fructose is converted is 5-keto-D-fructose. In some embodiments, the enzyme is 5-D-fructose dehydrogenase. In some embodiments, the composition of matter is a human dietary supplement or a pharmaceutical composition. In some embodiments, the composition of matter is an animal dietary supplement or a veterinary composition. In some embodiments, the composition is a special foodstuff. In some embodiments, the composition of matter further comprises at least one pharmaceutically or dietarily acceptable carrier or excipient. In some embodiments, the composition of matter further comprises at least one veterinarily acceptable carrier or excipient. In some embodiments, the composition of matter contains the enzyme in microencapsulated form. In some embodiments, the composition of matter is in the form of a capsule or tablet. In some embodiments, the composition of matter is in the form of granules or pellets. In some embodiments, the composition of matter is in the form of a solution. In some embodiments, the composition of matter is in the form of a liquid. In some embodiments, the composition of matter is in the form of a gel or suspension. In some embodiments, the composition of matter is in the form of a gelcap. In some embodiments, the composition of matter is in the form of a powder.

There is also provided, in accordance with embodiments of the invention, a composition of matter which is microencapsulated enzyme 5-D-fructose dehydrogenase.

In some embodiments, the composition of matter as described above is adapted to be mixed with a food.

There is also provided, in accordance with embodiments of the invention, a composition of matter comprising the enzyme 5-D-fructose dehydrogenase admixed with a mammalian-ingestible substance. In some embodiments, the mammalian-ingestible substance is a human-ingestible substance. In some embodiments, the mammalian-ingestible substance is an animal-ingestible substance. In some embodiments, the mammalian-ingestible substance is a pharmaceutically or dietarily acceptable carrier or excipient. In some embodiments, the mammalian-ingestible substance is a veterinarily acceptable carrier or excipient. In some embodiments, the 5-D-fructose dehydrogenase is microencapsulated.

In some embodiments, in the composition of matter as described above, the enzyme constitutes between 5 and 99.9% by weight of the composition of matter. In some embodiments, the enzyme constitutes between 10 and 80% by weight of the composition of matter. In some embodiments, the enzyme constitutes between 25 and 60% by weight of the composition of matter.

In some embodiments, the composition of matter as described above is in unit dosage form and the unit dosage contains between 10 and 5 million units of 5-D-fructose dehydrogenase activity. In some embodiments, the unit dosage contains between 25 and 2.5 million units of 5-D-fructose dehydrogenase activity. In some embodiments, the unit dosage contains between 50 and 1 million units of 5-D-fructose dehydrogenase activity.

In some embodiments, the composition of matter described above comprises a coating which dissolves in an aqueous medium at a pH of between 3.0 and 8.0. In some embodiments, the coating does not dissolve in an aqueous medium at a pH of below 3.0. In some embodiments, the coating does not dissolve in an aqueous medium at a pH below 4.0. In some embodiments, the coating does not dissolve in an aqueous medium at a pH above 6.5. In some embodiments, the coating does not dissolve in an aqueous medium at a pH above 6.0.

In some embodiments, the composition of matter as described above is a slow-release or extended-release formulation. In some embodiments, the slow-release or extended-release formulation comprises a slow-release or extended-release coating.

In some embodiments, the composition of matter as described above further comprises a second enzyme. In some embodiments, the second enzyme is capable of cleaving fructose or glucose from a sugar that contains at least two saccharide monomers. In some embodiments, the enzyme is invertase or maltase. In some embodiments, the second enzyme is invertase, the composition of matter is in unit dosage form, and each unit dosage contains between 50 and 250,000 Sumner units of invertase activity. In some embodiments, each unit dosage contains between 100 and 150,000 Sumner units of invertase activity. In some embodiments, each unit dosage contains between 150 and 100,000 Sumner units of invertase activity. In some embodiments, the second enzyme is maltase, the composition of matter is in unit dosage form, and each unit dosage contains between 100 and 100,000 units of maltase activity. In some embodiments, each unit dosage contains between 200 and 50,000 units of maltase activity. In some embodiments, each unit dosage contains between 500 and 20,000 units of maltase activity.

In some embodiments, the composition of matter as described above comprises both invertase and maltase.

In some embodiments, the composition of matter as described above further comprises an additional enzyme that converts D-fructose into a molecule that is absorbed more quickly than D-fructose from the intestine into the bloodstream. In some embodiments, the molecule is D-glucose.

In some embodiments, the composition of matter as described above further comprises an additional enzyme that converts D-glucose to D-fructose. In some embodiments, the additional enzyme is a glucose isomerase. In some embodiments, the composition of matter is in unit dosage form and each dosage unit contains 0.01 to 100,000 units of glucose isomerase activity per dose unit. In some embodiments, each dosage unit contains 0.05 to 10,000 units of glucose isomerase activity per dose unit. In some embodiments, each dosage unit contains 0.1 to 1,000 units of glucose isomerase activity per dose unit. In some embodiments, the glucose isomerase is a xylose isomerase.

In some embodiments, the composition of matter as described above further comprises one or more members of the group consisting of lactase, alpha-amylase, beta-amylase, glucoamylase, pullulanase, isoamylase, amyloglucosidase and cyclomaltodextrin glucantransferase (CGTase). In some embodiments, the member is lactase, the composition of matter is in unit dosage form and each dosage unit contains 50 to 200,000 FCC units of lactase activity per dose unit. In some embodiments, each dosage unit contains 100 to 100,000 FCC units of lactase activity per dose unit. In some embodiments, each dosage unit contains 150 to 50,000 units of lactase activity per dose unit.

In some embodiments, the composition of matter further comprises at least one of an electrolyte and a metal ion. In some embodiments, the electrolyte is selected from the group consisting of $MgSO_4$, $Na_2CO_3$, $NaHCO_3$, NaOH, $Na_2SO_4$, $MgCO_3$, $H_2SO_4$, $NaS_2O_3$, $NaS_2O_5$ and mixtures thereof. In some embodiments, the metal ion is selected from the group consisting of $Mn^{2+}$, $Mg^{2+}$, $Ca^{2+}$, $Zn^{2+}$, $Fe^{2+}$, $Co^{2+}$, $Cu^{2+}$ and mixtures thereof.

In accordance with some embodiments, the composition of matter is a foodstuff, and the enzyme is in active form. In some embodiments, the amount or concentration of the enzyme in the foodstuff is greater than the naturally occurring concentration or amount of the enzyme in the foodstuff. In some embodiments, the foodstuff is a fructose equivalent-containing foodstuff. In some embodiments, the foodstuff is a fructose-containing foodstuff. In some embodiments, the foodstuff is a glucose-containing foodstuff. In some embodiments, the enzyme is 5-D-fructose dehydrogenase which is present in an amount of 10 to 250,000 units of activity per gram of fructose in the foodstuff. In some embodiments, the 5-D-fructose dehydrogenase is present in an amount of 25 and 150,000 units of activity per gram of fructose in the foodstuff. In some embodiments, the 5-D-fructose dehydrogenase is present in an amount of 50 to 100,000 units of activity per gram of fructose in the foodstuff. In some embodiments, the foodstuff is a glucose-containing foodstuff and contains glucose isomerase in an amount of 0.01 to 20,000 units of activity per gram of glucose in the foodstuff. In some embodiments, the glucose isomerase is present in an amount of 0.05 to 10,000 units of activity per gram of glucose in the foodstuff. In some embodiments, the glucose isomerase is present in an amount of 0.1 to 1,000 units of activity per gram of glucose in the foodstuff. In some embodiments, the enzyme is 5-D-fructose dehydrogenase which is present in an amount of 10 to 250,000 units of activity per gram of total fructose in the foodstuff. In some embodiments, the 5-D-fructose dehydrogenase is present in an amount of 25 and 150,000 units of activity per gram of total fructose in the foodstuff. In some embodiments, the 5-D-fructose dehydrogenase is present in an amount of 50 to 100,000 units of activity per gram of total fructose in the foodstuff.

In some embodiments, the foodstuff is a foodstuff which has been baked. In some embodiments, the foodstuff is a foodstuff which has been cooked. In some embodiments, the foodstuff is a liquid, paste or broth. In some embodiments, the enzyme is present in the foodstuff in microencapsulated form. In some embodiments, the enzyme is 5-D-fructose dehydrogenase. In some embodiments, the foodstuff further contains a second enzyme in active form. In some embodiments, the concentration or amount of the second enzyme in the foodstuff is greater than the naturally occurring concentration or amount of the second enzyme in the foodstuff. In some embodiments, the second enzyme is selected from the group consisting of invertase, maltase, a glucose isomerase, lactase, alpha-amylase, beta-amylase, glucoamylase, pullulanase, isoamylase, amyloglucosidase and cyclomaltodextrin glucantransferase (CGTase) or a mixture thereof. In some embodiments, the second enzyme is invertase. In some embodiments, the second enzyme is maltase. In some embodiments, the second enzyme is lactase. In some embodiments, the second enzyme is alpha-amylase. In some embodiments, the second enzyme is beta-amylase. In some embodiments, the second enzyme is glucoamylase. In some embodiments, the second enzyme is pullulanase. In some embodiments, the second enzyme is isoamylase. In some embodiments, the second enzyme is amyloglucosidase. In some embodiments, the second enzyme is CGTase. In some embodiments, the second enzyme is a glucose isomerase. In some embodiments, the glucose isomerase is a xylose isomerase. In some embodiments, the composition of matter further comprises at least one of an electrolyte and a metal ion. In some embodiments, the electrolyte is selected from the group consisting of $MgSO_4$, $Na_2CO_3$, $NaHCO_3$, $NaOH$, $Na_2SO_4$, $MgCO_3$, $H_2SO_4$, $NaS_2O_3$, $NaS_2O_5$ and mixtures thereof. In some embodiments, the metal ion is selected from the group consisting of $Mn^{2+}$, $Mg^{2+}$, $Ca^{2+}$, $Zn^{2+}$, $Fe^{2+}$, $Co^{2+}$, $Cu^{2+}$ and mixtures thereof. In some embodiments, the second enzyme is a mixture of at least two of the group of invertase, maltase and a glucose isomerase. In some embodiments, the second enzyme is a mixture of at least two of the group of invertase, maltase, a glucose isomerase, lactase, amylase, beta-amylase, glucoamylase, pullulanase, isoamylase, amyloglucosidase and CGTase. In some embodiments, the second enzyme is in microencapsulated form.

In accordance with some embodiments, the composition of matter as described above comprises a mixture of enzymes that convert D-fructose into a form that is at least one of (a) biologically inactive in a chosen mammalian body, (b) not digestible in the digestive tract of said mammalian body and (c) not metabolizable in said mammalian body.

In accordance with some embodiments, the composition of matter as described above is a foodstuff which is not a dough.

In accordance with some embodiments, the enzyme that converts D-fructose into a form that is at least one of (a) biologically inactive in a chosen mammalian body, (b) not digestible in the digestive tract of said mammalian body and (c) not metabolizable in said mammalian body is not contained in an inorganic-based sol-gel biocompatible matrix.

In accordance with some embodiments, the composition of matter is substantially free of substances which are not approved for oral human ingestion. In accordance with some embodiments, the composition of matter is substantially free of substances which are not approved for oral non-human mammal ingestion.

In some embodiments, the composition of matter is adapted for oral ingestion.

In some embodiments, the composition of matter comprises an electron acceptor. In some embodiments, the electron acceptor is selected from the group consisting of Nicotinamide Adenine Dinucleotide+ (NAD+), nicotinamide adenine dinucleotide phosphate+ (NADP+), flavin adenine dinucleotide+ (FAD+), vitamin C, E or A, ferricyanide, ketones, aldehydes, 2,6-di-chloro-phenolindophenol, phenazine methsulfate and mixtures thereof. In some embodiments, the molar ratio of electron acceptor to total fructose is from 1:1 to 1:1000. In some embodiments, the molar ratio of electron acceptor to total fructose is from 1:2 to 1:200. In some embodiments, the molar ratio of electron acceptor to total fructose is from 1:10 to 1:50. In some embodiments, the molar ratio of electron acceptor to fructose is from 1:1 to 1:1000. In some embodiments, the molar ratio of electron acceptor to fructose is from 1:2 to 1:200. In some embodiments, the molar ratio of electron acceptor to fructose is from 1:10 to 1:50.

In accordance with some embodiments, the composition of matter further comprises one or more enzyme stabilizers. In some embodiments, the enzyme stabilizer stabilizes 5-D-fructose dehydrogenase. In some embodiments, the stabilizer stabilizes a glucose isomerase.

There is also provided, in accordance with embodiments of the invention, a method of treating adiposity in a mammalian subject body, comprising administering to a mammalian subject an efficacious amount of an enzyme or a mixture of enzymes that converts D-fructose into a form that is at least one of (a) biologically inactive in the subject body, (b) not digestible in the subject digestive tract and (c) not metabolizable in the subject body. There is also provided, in accordance with embodiments of the invention, a method of reducing the effect of D-fructose on a mammalian subject body, comprising administering to a mammalian subject an efficacious amount of an enzyme or a mixture of enzymes that converts D-fructose into a form that is at least one of (a) biologically inactive in the subject body, (b) not digestible in the subject digestive tract and (c) not metabolizable in the subject body. There is also provided, in accordance with embodiments of the invention, a method of reducing the effect of total fructose on a mammalian subject body, comprising administering to a mammalian subject an efficacious amount of an enzyme or a mixture of enzymes that converts total fructose into a form that is at least one of (a) biologically inactive in the subject body, (b) not digestible in the subject digestive tract and (c) not metabolizable in the subject body. In some embodiments, the mammalian subject is a human subject. In some embodiments, the mammalian subject is a non-human subject. In some embodiments, the administering comprises administering a mammalian-ingestible composition of matter as described above. In some embodiments, the effect of D-fructose or total fructose is adiposity. In some embodiments, the effect of D-fructose or total fructose is caloric intake via fructose metabolism. In some embodiments, the effect of D-fructose or total fructose is caloric intake via glucose metabolism. In some embodiments, the effect of D-fructose or total fructose is selected from the group consisting of (a) weight gain (b) acceleration of weight gain (c) the prevention of weight loss and (d) a lessening of the rate of weight loss. In some embodiments, the effect of D-fructose or total fructose is a deleterious effect on the weight or health of said mammal. In some embodiments, the adiposity is treated post-facto. In some embodiments, the adiposity is reduced or prevented prophylactically. In some embodiments, the composition of matter is administered prior to eating. In some embodiments, the composition of matter is administered immediately prior to eating. In some embodiments, the composition of matter is administered concurrently with a meal. In some embodiments, the composition of matter is administered after eating. In some embodiments, the composition of matter is administered immediately after eating. In some embodiments, the form is into which D-fructose is converted is 5-keto-D-fructose. In some embodiments, the method is used as part of a program of therapeutic or prophylactic treatment of at least one of the following, alone or attendant to adiposity: cardiovascular disease, a disease or disorder of metabolic function, a disease or disorder of hormonal function, respiratory disease or disorder, disease or disorder of the hepatobiliary system, disease or disorder of the locomotor system, disease or disorder of the skin, neoplasias associated with adiposity, disorder of sexual function, psychosocial problems, reduced mobility, reduced stamina, and fatigue. In some embodiments, the cardiovascular disease is selected from the group consisting of hypertension, coronary heart disease, venous insufficiency, heart failure, left-ventricular hypertrophy and arteriosclerosis. In some embodiments, the disease or disorder of metabolic function is selected from the group consisting of diabetes mellitus type II, dyslipidemias, hyperuricemia and hyperlipoproteinemia. In some embodiments, the respiratory disease or disorder is sleep apnea or Pickwickan syndrome. In some embodiments, the disease or disorder of the hepatobiliary system is fatty liver or cholecystolithiasis. In some embodiments, the disease or disorder of the locomotor system is selected from the group consisting of gonarthrosis, heel spur and arthrosis of the ankle joint. In some embodiments, the disease or disorder of the skin is selected from the group consisting of intertrigo, hirsutism and striae. In some embodiments, the neoplasias are selected from the group consisting of endometrial, mama, cervix and gall bladder carcinoma. In some embodiments, the disorder of sexual function is reduced fertility or an increased risk of complications during birth. In some embodiments, the psychosocial problems are selected from the group consisting of reduced self-confidence, social isolation, discrimination, problems with the partner and problems at the job. In some embodiments, the method further comprises administering to the subject a second enzyme selected from the group consisting of invertase, maltase, a glucose isomerase, lactase, alpha-amylase, beta-amylase, glucoamylase, pullulanase, isoamylase, amyloglucosidase and cyclomaltodextrin glucantransferase (CGTase) or a mixture thereof.

There is also provided, in accordance with embodiments of the invention, a kit comprising an enzyme that converts D-fructose into a form that is at least one of (a) biologically inactive in a chosen mammalian body, (b) not digestible in the digestive tract of said mammalian body and (c) not metabolizable in said mammalian body, or a mixture of such enzymes, and instructions explaining how to use said enzyme or mixture thereof to reduce the effects of fructose in said mammalian body. In some embodiments, the instructions explain how to use said enzyme or mixture thereof to reduce the effects of total fructose in said mammalian body. In some embodiments, the mammalian body is the human body. In some embodiments, the mammalian body is a non-human body. In some embodiments, the enzyme or mixture thereof is present as a composition of matter as described above. In some embodiments, the enzyme or mixture of enzymes converts D-fructose into 5-keto-D-fructose. In some embodiments, the enzyme is 5-D-fructose dehydrogenase. In some embodiments, the kit further comprises a second enzyme. In some embodiments, the second enzyme is selected from the group consisting of invertase, maltase, a glucose isomerase, lactase, alpha-amylase, beta-amylase, glucoamylase, pullulanase, isoamylase, amyloglucosidase and cyclomaltodextrin glucantransferase (CGTase) or a mixture thereof. In some embodiments, the second enzyme is a glucose isomerase. In some embodiments, the instructions further explain how to use the second enzyme or mixture thereof in conjunction with the enzyme. In some embodiments, the instructions explain how to use a mixture of the second enzyme and the enzyme.

The invention claimed is:

1. A mammalian ingestible composition which is adapted for oral administration selected from a pharmaceutical composition and a dietary supplement, said composition being in unit dosage form and is selected from the group consisting of a tablet, capsule, gel cap and dragée, said composition comprising 5-D-fructose dehydrogenase and a carrier or excipient that is acceptable for use in pharmaceutical compositions or foodstuffs, said composition further comprising a second enzyme selected from the group consisting of a glucose isomerase, lactase, alpha-amylase, beta-amylase, glucoamylase, pullulanase, isoamylase, amyloglucosidase, cyclomaltodextrine glucanotransferase, and mixtures thereof, wherein said 5-D-fructose dehydrogenase constitutes between 10 and 99.9% by weight of the composition.

2. The composition according to claim 1 wherein said 5-D-fructose dehydrogenase is protected by a coating which is stable at a pH below 4.

3. The composition according to claim 2 wherein said coating protects the entire dosage unit.

4. The composition according to claim 1 wherein said 5-D-fructose dehydrogenase is microencapsulated.

5. The composition according to claim 1 wherein said unit dosage contains between 50 and 1 million units of 5-D-fructose dehydrogenase activity.

6. The composition according to claim 1 wherein said composition comprises a coating which dissolves at a pH of 5.5 or higher.

7. The composition according to claim 1 wherein said 5-D-fructose dehydrogenase is not contained in an inorganic-based sol-gel biocompatible matrix.

8. The composition according to claim 1 wherein said second enzyme is a glucose isomerase.

9. The composition according to claim 8, further comprising a third enzyme selected from the group consisting of invertase, maltase, lactase, alpha-amylase, beta-amylase, glucoamylase, pullulanase, isoamylase, amyloglucosidase, cyclomaltodextrin glucanotransferase and mixtures thereof.

10. The composition according to claim 1, wherein said second enzyme is selected from the group consisting of lactase, alpha-amylase, beta-amylase, glucoamylase, pullulanase, isoamylase, amyloglucosidase, cyclomaltodextrin glucanotransferase and mixtures thereof.

11. The composition according to claim 1 wherein said 5-D-fructose dehydrogenase constitutes between 25 and 60% by weight of the composition.

12. The composition according to claim 1 wherein said 5-D-fructose dehydrogenase constitutes between 10 and 80% by weight of the composition.

13. A method of treating adiposity, reducing the effect of adiposity on a mammalian body, reducing the effect of D-fructose in a mammalian body, or reducing the effect of total fructose in a mammalian body, comprising administering to a subject in need of such treatment or reduction an efficacious amount of a mammalian ingestible composition according to claim 1.

14. The method according to claim 13 wherein said 5-D-fructose dehydrogenase is protected by a coating which is stable at a pH below 4.

15. The method according to claim 14 wherein said coating protects the entire dosage unit.

16. The method according to claim 13 wherein said 5-D-fructose dehydrogenase is microencapsulated.

17. The method according to claim 13 wherein said unit dosage contains between 50 and 1 million units of 5-D-fructose dehydrogenase activity.

18. The method according to claim 13 wherein said composition comprises a coating which dissolves at a pH of 5.5 or higher.

19. The method according to claim 13 wherein said second enzyme is a glucose isomerase.

20. The method according to claim 19, further comprising a third enzyme selected from the group consisting of invertase, maltase, lactase, alpha-amylase, beta-amylase, glucoamylase, pullulanase, isoamylase, amyloglucosidase, cyclomaltodextrin glucanotransferase and mixtures thereof.

* * * * *